US00PP30632P3

(12) United States Plant Patent
Layt

(10) Patent No.: US PP30,632 P3
(45) Date of Patent: Jul. 2, 2019

(54) ***SYZYGIUM* PLANT NAMED 'SAN01'**

(50) Latin Name: *Syzygium australe*
Varietal Denomination: SAN01

(71) Applicant: Todd Anthony Layt, Clarendon (AU)

(72) Inventor: Todd Anthony Layt, Clarendon (AU)

( * ) Notice: Subject to any disclaimer, the term of this patent is extended or adjusted under 35 U.S.C. 154(b) by 0 days.

(21) Appl. No.: 15/932,023

(22) Filed: Jan. 25, 2018

(65) Prior Publication Data

US 2018/0213698 P1 Jul. 26, 2018

(30) Foreign Application Priority Data

Jan. 26, 2017 (AU) ..... PBR 2017/012

(51) Int. Cl.
*A01H 5/00* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
See application file for complete search history.

*Primary Examiner* — Susan McCormick Ewoldt
(74) *Attorney, Agent, or Firm* — Samuel R. McCoy, Jr.

(57) ABSTRACT

A new and distinct *Syzygium* cultivar named 'SAN01' which is characterized by the combination of a fastigiate growth habit, dense foliage, excellent resistance to psyllid, and the stability of these characteristics from generation to generation.

1 Drawing Sheet

Latin name of the genus and species: The Latin name of the genus and species of the novel variety disclosed herein is *Syzygium australe.*

Variety denomination: The inventive cultivar of *Syzygium* disclosed herein has been given the variety denomination 'SAN01'.

CROSS REFERENCE TO RELATED APPLICATIONS

This application claims priority to the Australian Plant Breeders Rights application number 2017/012, filed on Jan. 26, 2017, which is herein incorporated by reference.

BACKGROUND OF THE INVENTION

Parentage: 'SAN01' originated as a seedling selection which resulted from the open pollination of an unnamed *Syzygium australe* plant (not patented) with an upright globular plant form. The breeding process occurred at a plant breeding facility in Clarendon, New South Wales, Australia. The pollen parent is unknown. In January of 2011, seed was harvested from the parent and germinated. Approximately 300 resulting seedlings were potted into nursery containers and grown to maturity in order to evaluate for desirable commercial attributes. In particular, the breeder desired to select a new *Syzygium* variety which exhibited a narrowly fastigiate growth habit, dense foliage, and improved resistance to psyllid (*Trioza eugeniae*). Of the original 300 seedlings, 50 were observed to exhibit a growth habit more erect than that of the seed parent. These seedlings were subsequently isolated for continued evaluation and, in February of 2013, 30 of the 50 seedlings were determined to possess a narrowly fastigiate growth habit. These 30 candidates were further observed to evaluate vigor and psyllid resistance. After further evaluation, one plant was determined to exhibit the desired combination of a fastigiate growth habit, dense foliage, and psyllid resistance. The new plant was given the denomination, 'SAN01'.

Asexual Reproduction: Asexual reproduction of 'SAN01', by way of semi-hardwood stem cuttings, was first performed in 2014 in Clarendon, New South Wales, Australia. Through five subsequent generations, the unique features of this cultivar have proven to be stable and true to type.

SUMMARY OF THE INVENTION

The cultivar 'SAN01' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SAN01'. These characteristics in combination distinguish 'SAN01' as a new and distinct *Syzygium* cultivar:

1. *Syzygium* 'SAN01' exhibits a narrowly fastigiate growth habit; and
2. *Syzygium* 'SAN01' exhibits dense foliage; and
3. *Syzygium* 'SAN01' exhibits excellent resistance to psyllid (*Trioza eugeniae*).

BRIEF DESCRIPTION OF THE FIGURES

The accompanying color drawing illustrates, as nearly true as it is reasonably possible to make the same in color photographs of this type, an exemplary 3 year old 'SAN01' plant grown outdoors in a 10 inch nursery container at a breeding facility in Clarendon, New South Wales, Australia.

BOTANICAL DESCRIPTION OF THE PLANT

The following observations and measurements made in October of 2017 and, unless otherwise indicated, describe a 24 month old 'SAN01' plant which was grown outdoors in a 10 inch container in Clarendon, New South Wales, Australia. Plants were produced in full sun, using conventional production protocols for *Syzygium* which consisted of regular overhead irrigation and controlled-release fertilizer applications. No chemical pest or disease measures were utilized in production.

Those skilled in the art will appreciate that certain characteristics will vary with older or, conversely, with younger plants. 'SAN01' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2001 edition.

A botanical description of 'SAN01' and a comparison with the parent plant and the most similar commercial *Syzygium* cultivar known to the inventor, is provided below.

Plant description:

*Growth habit.*—Fastigiate shrub to small tree.

*Average height.*—85 cm as observed.

*Average width.*—32 cm as observed.

*Plant vigor.*—Moderately vigorous.

*Propagation details.*—Asexual propagation may be accomplished by semi-hardwood stem cuttings.

*Time to produce a marketable rooted cutting.*—Approximately 8 weeks when propagated in the spring.

*Time to produce a marketable finished plant.*—Approximately 18 to 24 months are required to produce a marketable 10 inch nursery container, depending on climate and cultural production practices.

*Disease and pest resistance or susceptibility.*—Excellent resistance to psyllid (*Trioza eugeniae*). Neither tolerance nor resistance to other diseases and pests of *Syzygium* have been observed.

*Environmental tolerances.*—Hardy to approximately 0 degrees Celsius and tolerant of temperatures to 40 degrees Celsius. Generally drought tolerant once established.

Root system:

*General.*—Fibrous; freely branched and moderately dense rooting.

*Distribution in the soil profile.*—Shallow to moderately deep.

*Texture.*—Smooth.

*Color, juvenile roots.*—Orange-white, nearest to RHS 158D.

*Color, mature roots.*—Greyed-brown, nearest to RHS 165A.

Stems:

*Branching habit.*—One main stem, itself freely branching, and giving rise to numerous lateral branches. Lateral branching occurs from very near the base of the main stem to the apex.

*Main stem.*—Attitude — Erect. Diameter — 25 mm at the base. Internode length — 22 mm. Shape — Round. Strength — Strong. Texture, juvenile and mature portions of the main stem — Smooth. Color, juvenile portion of main stem — Greyed-purple, nearest to a mixture of RHS 183A and 183B. Color, mature portion of main stem — Nearest to a mixture of yellow-green, RHS 146C, and greyed-orange, RHS 166A. Texture of the oldest wood — Fissured. Color of the oldest wood — Greyed-brown, RHS 199B.

*Lateral branches.*—Aspect — Erect. Shape — Rounded. Strength — Weak to moderately strong. Diameter of lateral branches — Averaging 15 mm at the base. Internode length on lateral branches — Approximately 33 mm. Texture — Smooth. Color, juvenile portion of lateral branches — Greyed-purple, nearest to a mixture of RHS 183A and 183B. Color, mature portion of lateral branches — Nearest to a mixture of yellow-green, RHS 146C, and greyed-orange, RHS 166A.

Foliage:

*Arrangement.*—Opposite.

*Attachment.*—Petiolate.

*Division.*—Simple.

*Foliage density on lateral branch.*—Very dense.

*Foliage attitude.*—Outward.

*Lamina.*—Dimensions — 38 mm long and 17 mm wide, on average. Thickness — Approximately 1 mm. Shape — Elliptic. Aspect — Involute. Apex — Acute. Base — Acute. Margin — Entire; lightly undulated. Pubescence, adaxial surface — Glabrous. Texture and luster of adaxial surface — Smooth and matte to semi-glossy. Pubescence, abaxial surface — Glabrous. Texture and luster of abaxial surface — Smooth and matte to semi-glossy. Color — Juvenile foliage, adaxial surface — Yellow-green, RHS 146B; newly emerged foliage is lightly suffused with yellow-orange, RHS 22A. Juvenile foliage, abaxial surface — Yellow-green, RHS 146C; newly emerged foliage is very lightly suffused with yellow-orange, RHS 22A. Mature foliage, adaxial surface — Green, RHS 137A. Mature foliage, abaxial surface — Yellow-green, RHS 146B. Venation — Pattern — Pinnate. Color, adaxial surface — Green, RHS 137A. Color, abaxial surface — Yellow-green, RHS 146B.

*Petiole.*—Length — 3.5 mm. Width — 1.0 mm. Texture — Glabrous; smooth. Luster — Semi-glossy. Color, juvenile foliage — Yellow-green, RHS 146A. Color, mature foliage — Green, RHS 137A.

Inflorescence: No flowering has been observed to date.

Flower buds: No flowering has been observed to date.

Flower: No flowering has been observed to date.

Reproductive organs: Not observed.

Seed and fruit: Not observed.

Comparison with the parent: Plants of the new cultivar 'SAN01' may be distinguished from its parent, an unnamed *Syzygium australe* plant (not patented), by the characteristics described in Table 1.

TABLE 1

| Characteristic | 'SAN01' | The seed parent. |
|---|---|---|
| Growth habit. | Narrowly fastigiate. | Upright globular. |
| Psyllid resistance. | Excellent resistance. | Not resistant. |
| Abundance of foliage. | More abundant than the seed parent. | Less abundant than 'SAN01'. |

Comparison with the closest known commercial comparator: Plants of the new cultivar 'SAN01' may be distinguished from the most similar known commercial comparator, *Syzygium* 'AATS' (abandoned U.S. patent application Ser. No. 12/156,973), by the characteristics described in Table 2.

TABLE 2

| Characteristic | 'SAN01' | 'AATS' |
|---|---|---|
| Growth habit. | Narrowly fastigiated. | Columnar. |
| Basal branching. | Freely branching from the base. | More sparsley branching from the base. |

That which is claimed is:

1. A new and distinct cultivar of *Syzygium* plant named 'SAN01', substantially as described and illustrated herein.

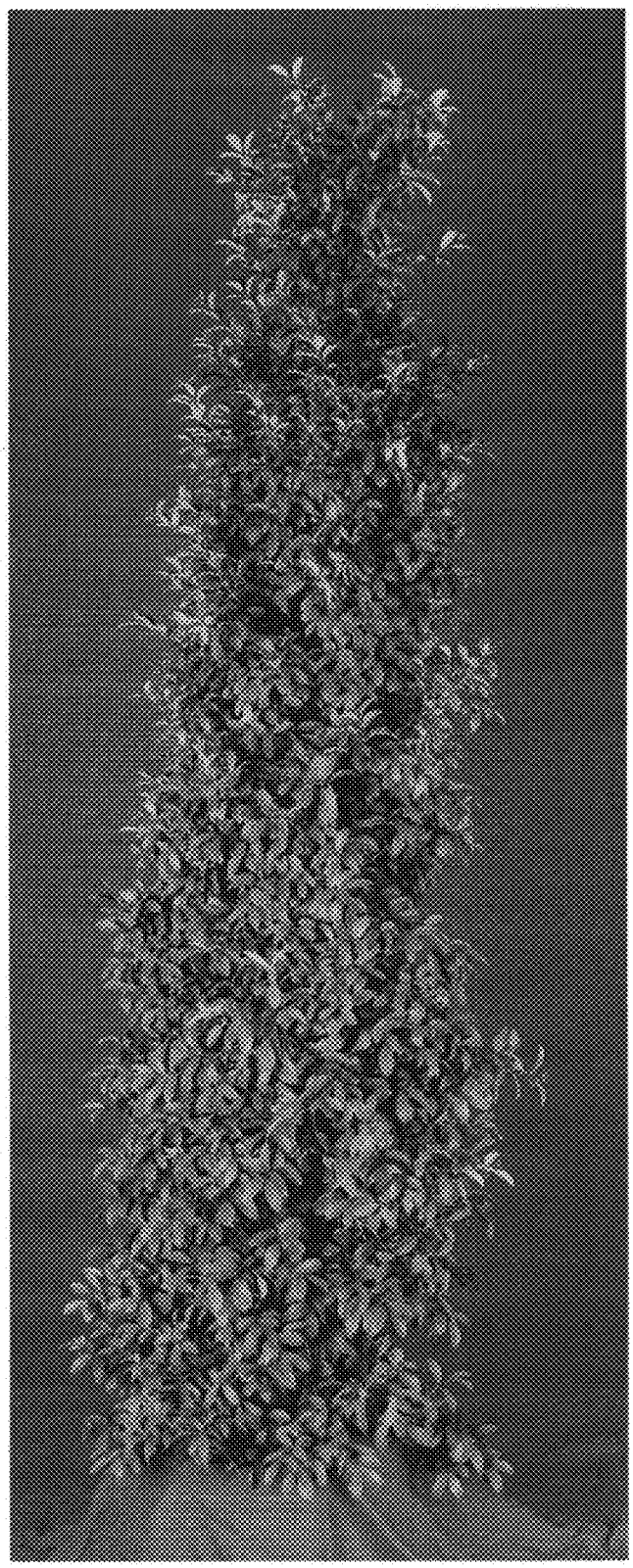

* * * * *